United States Patent
Brown et al.

(10) Patent No.: US 12,029,701 B2
(45) Date of Patent: *Jul. 9, 2024

(54) AURICULAR PERIPHERAL NERVE FIELD STIMULATOR AND METHOD OF OPERATING SAME

(71) Applicant: Neuraxis, Inc., Versailles, IN (US)

(72) Inventors: Christopher R. Brown, Greensburg, IN (US); Gary M. Peterson, Versailles, IN (US)

(73) Assignee: Neuraxis, Inc., Versailles, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,375

(22) Filed: Jan. 13, 2023

(65) Prior Publication Data
US 2023/0190577 A1 Jun. 22, 2023

Related U.S. Application Data

(63) Continuation of application No. 17/363,620, filed on Jun. 30, 2021, now Pat. No. 11,654,082, which is a
(Continued)

(51) Int. Cl.
*A61N 1/36* (2006.01)
*A61H 39/00* (2006.01)
(Continued)

(52) U.S. Cl.
CPC ........... *A61H 39/002* (2013.01); *A61H 39/02* (2013.01); *A61N 1/0551* (2013.01);
(Continued)

(58) Field of Classification Search
CPC .................................................. A61H 39/002
(Continued)

(56) References Cited

U.S. PATENT DOCUMENTS

4,305,402 A 12/1981 Katims
4,646,744 A 3/1987 Capel
(Continued)

FOREIGN PATENT DOCUMENTS

AT 395106 2/1992
EP 1335774 8/2003
(Continued)

OTHER PUBLICATIONS

First Office Action issued in co-pending Japanese Application No. 2021-50996, dated of Dec. 22, 2022.
(Continued)

*Primary Examiner* — Nadia A Mahmood
(74) *Attorney, Agent, or Firm* — Barnes & Thornburg LLP

(57) ABSTRACT

An auricular peripheral nerve field stimulator may include at least one therapy electrode configured for percutaneous insertion into an auricle of a human ear near at least one neurovascular bundle located therein, and an electrical stimulation device electrically coupled to the electrical stimulation device, the electrical stimulation device programmed to generate and deliver electrical stimulation signals, with defined stimulation parameters, to the at least one therapy electrode to stimulate, with the at least one therapy electrode percutaneously inserted, at least one auricular peripheral nerve field within the auricle, the defined stimulation parameters including a defined pulse frequency and at least one of a defined pulse width and a defined duty cycle.

20 Claims, 10 Drawing Sheets

Related U.S. Application Data continuation of application No. 16/408,004, filed on May 9, 2019, now Pat. No. 11,077,019, which is a continuation of application No. 16/014,169, filed on Jun. 21, 2018, now Pat. No. 10,322,062, which is a continuation of application No. 15/811,278, filed on Nov. 13, 2017, now Pat. No. 10,010,479, which is a continuation of application No. 15/595,185, filed on May 15, 2017, now Pat. No. 9,839,577, which is a continuation of application No. 14/277,158, filed on May 14, 2014, now Pat. No. 9,662,269.

(60) Provisional application No. 61/894,270, filed on Oct. 22, 2013.

(51) Int. Cl.
*A61H 39/02* (2006.01)
*A61N 1/05* (2006.01)

(52) U.S. Cl.
CPC .. *A61N 1/36135* (2013.01); *A61H 2201/5005* (2013.01); *A61H 2201/5007* (2013.01); *A61H 2201/5023* (2013.01); *A61H 2201/5033* (2013.01); *A61H 2201/5038* (2013.01); *A61H 2201/5058* (2013.01); *A61H 2205/027* (2013.01); *A61H 2230/105* (2013.01); *A61H 2230/405* (2013.01); *A61H 2230/505* (2013.01); *A61H 2230/605* (2013.01)

(58) Field of Classification Search
USPC .......................................................... 607/46
See application file for complete search history.

(56) References Cited

U.S. PATENT DOCUMENTS

| | | | |
|---|---|---|---|
| 4,865,048 A * | 9/1989 | Eckerson | A61N 1/36025 607/45 |
| 5,084,007 A | 1/1992 | Malin | |
| 5,094,242 A | 3/1992 | Gleason | |
| 5,458,625 A | 10/1995 | Kendall | |
| 6,296,652 B1 | 1/2001 | Qingmin | |
| 6,212,433 B1 | 4/2001 | Behl | |
| 7,092,849 B2 | 8/2006 | Lafitte | |
| 7,103,417 B1 | 9/2006 | Segel | |
| 7,660,637 B2 | 2/2010 | Szeles | |
| 8,308,784 B2 | 11/2012 | Streeter | |
| 8,428,719 B2 | 4/2013 | Napadow | |
| 8,465,531 B2 | 6/2013 | Aunio | |
| 8,535,361 B2 | 9/2013 | Lim | |
| 8,761,872 B2 | 6/2014 | Hinrichsen | |
| 8,942,814 B2 | 1/2015 | Szeles | |
| 9,662,269 B2 | 5/2017 | Brown | |
| 9,782,584 B2 | 10/2017 | Cartledge | |
| 9,839,577 B2 | 12/2017 | Brown | |
| 9,901,734 B2 | 2/2018 | Bennett | |
| 10,010,479 B2 | 3/2018 | Brown | |
| 10,052,257 B2 | 8/2018 | Nageshwar | |
| 10,058,478 B2 | 8/2018 | Schnetz | |
| 10,086,199 B2 | 10/2018 | Robertson | |
| 10,130,275 B2 | 11/2018 | Nageshwar | |
| 10,130,809 B2 | 11/2018 | Cartledge | |
| 10,413,719 B2 | 9/2019 | Brown | |
| 10,471,276 B2 | 11/2019 | Beckner | |
| 10,695,568 B1 | 6/2020 | Covalin | |
| 10,806,928 B2 | 10/2020 | Sharma | |
| 2003/0050470 A1 | 3/2003 | An | |
| 2003/0149451 A1 | 8/2003 | Chomenky | |
| 2004/0044390 A1 | 3/2004 | Szeles | |
| 2006/0122675 A1 | 6/2006 | Libbus | |
| 2007/0198063 A1 | 8/2007 | Hunter | |
| 2008/0051852 A1 | 2/2008 | Dietrich | |
| 2008/0146549 A1 | 6/2008 | Coleman | |
| 2008/0249439 A1 | 10/2008 | Tracey | |
| 2010/0004715 A1 | 1/2010 | Fahey | |
| 2010/0113965 A1 | 5/2010 | Kanevsky | |
| 2010/0168822 A1 | 7/2010 | Szeles | |
| 2010/0262205 A1 | 10/2010 | De Ridder | |
| 2011/0160811 A1 | 6/2011 | Walker | |
| 2011/0190569 A1 | 8/2011 | Simon | |
| 2012/0226333 A1 | 9/2012 | Szeles | |
| 2012/0253427 A1 | 10/2012 | Aunio | |
| 2013/0150923 A1 * | 6/2013 | Schnetz | A61N 1/36034 607/59 |
| 2014/0081368 A1 | 3/2014 | Szeles | |
| 2014/0370476 A1 | 12/2014 | Nageshwar | |
| 2014/0371608 A1 | 12/2014 | Nageshwar | |
| 2014/0371621 A1 | 12/2014 | Nageshwar | |
| 2015/0112405 A1 | 4/2015 | Brown | |
| 2015/0112411 A1 | 4/2015 | Beckman | |
| 2015/0265830 A1 | 9/2015 | Simon | |
| 2016/0074663 A1 | 3/2016 | De Ridder | |
| 2016/0113526 A1 | 4/2016 | Nageshwar | |
| 2016/0144175 A1 | 5/2016 | Simon | |
| 2017/0143247 A1 | 5/2017 | Nageshwar | |
| 2017/0197081 A1 | 7/2017 | Charlesworth | |
| 2018/0064603 A1 | 3/2018 | Brown | |
| 2018/0256917 A9 | 9/2018 | Lim | |
| 2018/0280721 A1 | 10/2018 | Beckner | |
| 2018/0296435 A1 | 10/2018 | Brown | |
| 2019/0262229 A1 | 8/2019 | Brown | |

FOREIGN PATENT DOCUMENTS

| | | |
|---|---|---|
| EP | 2474339 | 11/2012 |
| WO | 2005001706 | 1/2005 |
| WO | 2011030210 | 3/2011 |
| WO | 2014200488 | 12/2014 |
| WO | 2014200489 | 12/2014 |
| WO | 2014200492 | 12/2014 |
| WO | 2014200498 | 12/2014 |
| WO | 2014207512 | 12/2014 |
| WO | 2015008154 | 1/2015 |
| WO | 2016151377 | 9/2016 |
| WO | 2019053625 A1 | 3/2019 |

OTHER PUBLICATIONS

International Search Report prepared for PCT/US2019/029172 mailed Jan. 28, 2020.

Extended Eurpean Search Report in Application No. 19850021.7-122 dated Dec. 17, 2021.

International Search Report prepared for PCT/US2020/039040 mailed Sep. 11, 2020.

Garcia-Argibay, M. et al., "Efficacy of binaural auditory beats in congnition, anxiety, and pain perception: a meta-analysis," Psychological Research, Aug. 2, 2018, vol. 83, pp. 357-372.

Palaniappan, R. et al., "On the binaural brain entrainment indicating lower heart rate variability," Cardiology, 2015, vol. 190, pp. 262-263.

Kim, Byunghyun et al., "The Effect of White Noise and Pink Noise on the Brain Activity," The Journal of the Korea Contents Association, 2017, 17(5) pp. 491-498. (English machine-translation appended).

Da Silva, V.F. et al., "Stimulation by Light and Sound: Therapeutic Effects in Humans. Systematic Review," Clin Pract Epidemiol Ment Health, 2015, vol. 11, p. 150-4.

Gkolias, V. et al., "Reduced pain and analgesic use after acoustic binaural beats therapy in chronic pain—A double-blind randomized control cross-over trial," European J. Pain, 2020, 24(9) pp. 1716-1729.

Perez, H.D.O. et al., "Binaural Beats through the Auitory Pathway: From Brainstem to Connectivity Patterns," eNeuro, 2020, 7(2) 29 pages.

McConnel, P.A. et al., "Auditory driving of the autonomic nervous system: Listening to theta-frequency binaural beats post-exercise increases parasympathetic activation and sympathetic withdrawal," Frontiers in Psychology, 2014, vol. 5, 10 pages.

(56) References Cited

OTHER PUBLICATIONS

Graham, M.T. et al., "Simulations and human cadaver head studies to identify optimal acoustic receiver locations for minimally invasive photoacoustic-guided neurosurgery," Photoacoustics, 2020, 14 pages.
Grose, J.H. et. al., "Binaural beat salience," Hear Res, 2013, 285(1-2) pp. 40-45.
Chaieb, L. et al., "Auditory beat stimulation and its effects on cognition and mood states," Frontiers in Psychiatry, 2015, vol. 6, pp. 1-9.
Ablen, V. et al., "Brainwave entrainment for better sleep and post-sleep state of young elite soccer players-study," European Journal of Sport Science, 2014, 14(5) pp. 393-402.
Wei, Q. et al., "Novel design of smart sleep-lighting system for improving the sleep environment of children," Technology and Health Care, 2019, vol. 27, pp. S3-S13.
Seshagiri, C.V. et al., "Response Properties of Neighboring Neurons in the Auditory Midbrain for Pure-Tone Stimulation: A Tetrode Study," J. Neurophysiol., 2007, vol. 98, pp. 2058-2073.
Padmanabhan, R. et al., "A prospective, randomised, controlled study examining binaural beat audio and pre-operative anxiety in patients undergoing general anaesthesia for day case surgery," Anasthesia, 2005, 60(9) pp. 874-877.
Non-Final Office Action dated Mar. 19, 2018 filed in U.S. Pat. No. 10,010,479 issued Jul. 3, 2018.
Response and Terminal Disclaimer filed Apr. 10, 2018 to Non-Final Office Action dated Mar. 19, 2018 in U.S. Pat. No. 10,010,479 issued Jul. 3, 2018.
Non-Final Office Action dated Aug. 2, 2017 filed in U.S. Pat. No. 9,839,577 issued Dec. 12, 2017.
Response and Terminal Disclaimer filed Sep. 7, 2017 to Non-Final Office Action dated Aug. 2, 2017 in U.S. Pat. No. 9,839,577 issued Dec. 12, 2017.
Non-Final Office Action dated Jul. 15, 2015 filed in U.S. Pat. No. 9,662,269 issued May 30, 2017.
Response filed Nov. 16, 2015 to Non-Final Office Action dated Jul. 15, 2015 in U.S. Pat. No. 9,662,269 issued May 30, 2017.
Final Office Action dated Feb. 25, 2016 filed in U.S. Pat. No. 9,662,269 issued May 30, 2017.
Response and Request for Continued Examination filed Jun. 27, 2016 to Final Office Action dated Feb. 25, 2016 in U.S. Pat. No. 9,662,269 issued May 30, 2017.
Non-Final Office Action dated Jul. 28, 2016 filed in U.S. Pat. No. 9,662,269 issued May 30, 2017.
Response filed Aug. 25, 2016 to Non-Final Office Action dated Jul. 28, 2016 in U.S. Pat. No. 9,662,269 issued May 30, 2017.
Non-Final Office Action dated Dec. 1, 2016 filed in U.S. Pat. No. 9,662,269 issued May 30, 2017.
Response filed Feb. 27, 2017 to Non-Final Office Action dated Dec. 1, 2016 in U.S. Pat. No. 9,662,269 issued May 30, 2017.
Roberts, Arthur and Christopher R. Brown. "Percutaneous Peri-Auricular Peripheral Nerve Field Stimulation: A Novel, Non-Opioid Therapy for Diabetic Neuropathy." The Pain Practitioner, vol. 25, 3 (2015): 41-47.

* cited by examiner

AURICULAR PERIPHERAL NERVE FIELD STIMULATOR AND METHOD OF OPERATING SAME

CROSS-REFERENCE TO RELATED APPLICATIONS

This patent application is a continuation of U.S. patent application Ser. No. 17/363,620, filed Jun. 30, 2021, which is a continuation of U.S. patent application Ser. No. 16/408,004, filed May 9, 2019 and now U.S. Pat. No. 11,077,019, which is a continuation of U.S. patent application Ser. No. 16/014,169, filed Jun. 21, 2018 and now U.S. Pat. No. 10,322,062, which is a continuation of U.S. patent application Ser. No. 15/811,278, filed Nov. 13, 2017 and now U.S. Pat. No. 10,010,479, which is a continuation of U.S. patent application Ser. No. 15/595,185, filed May 15, 2017 and now U.S. Pat. No. 9,839,577, which is a continuation of U.S. patent application Ser. No. 14/277,158, filed May 14, 2014 and now U.S. Pat. No. 9,662,269, which claims the benefit of, and priority to, U.S. Provisional Patent Application Ser. No. 61/894,270, the disclosures of which are all incorporated herein by reference in their entireties.

BACKGROUND OF THE INVENTION

1. Field of the Invention

The field of art disclosed herein pertains to an electrical stimulation device including a stimulator containing a generator for generating electrical stimulation pulses with defined stimulation parameters and a power supply for supplying the generator with electrical energy, and at least one needle electrode array for insertion into the skin surface of an area to be stimulated.

2. Description of the Related Art

An electrical stimulation device of the present type is, for instance, known from AT 395 106 B and EP 1 335 774 B1. The electrical stimulation devices are used in the electrical acupuncture therapy of humans and animals. Often, the devices are suitable for using the electrical stimulation of acupuncture points in the region of the ear. Applications range from pain management to wound healing, to therapies of circulatory disorders, e.g. in diabetes.

Placement of acupuncture needles, both electrically and non-electrically stimulated in the auricular (ear) anatomy has been used for pain control for decades. The theory for effectiveness of acupuncture has been based upon theories, which include energy flow (chi), application of heat or cold and the use of reflex points The actual location and determination of needle placement (called points) is based upon tradition and theory of acupuncture. While the ascribed "points" may vary, depending upon the type of acupuncture to which one prescribes, the rationale and needle placement varies little and the theory is the same.

The addition of electrical stimulation to the individual, non-connected needles does not alter the rationale and the location of application is still based upon the original theory. The addition of electricity, while considered an enhancement, still falls within the realm of auricular acupuncture.

Peripheral nerve field stimulation is an accepted procedure for the affecting of targeted nerves to alter pain transmission on a local (peripheral) and CNS (central nervous system) level. PNFS is commonly used in the occipital nerves (branches of the cervical nerves) for headache control, and the femoral nerve of the leg for control of phantom limb pain, stump pain, and other types of pain, including pre and post surgical pain and acute and chronic pain.

The PNFS technique is based upon neuro-anatomy, blood vessel anatomy, the proximity of the electrodes to the actual nerves being stimulated and verification of electrode proximity Located within the ear are cranial nerves V, VII, IX, X which anastomose (connect) directly into the brain and branches of the greater and lesser occipital nerves anastomosing directly into the cervical spine. There are distinct areas of the auricle on both the dorsal and ventral aspect which carry a predominance/concentration of the cranial nerves, peripheral nerves, arterial branches, and neurovascular bundles.

Branches of the superior temporal artery and the posterior auricular artery are found within the external ear, entering from the anterior (ventral) and posterior (dorsal) aspect of the ear. These arteries converge in the lobe, branching eventually into the cellular level forming a complex, interconnecting network branching according to Mandelbrot's set.

The present invention provides for a system and methods not based upon acupuncture technique or "points" but rather peripheral nerve field stimulation, anatomical location of cranial nerves, peripheral nerves, arterial branches and/or neurovascular bundles, and energy transfer based upon accepted laws of energy transfer in human tissue. These physical entities can be selectively targeted by percutaneous implantation of one or more electrode-needle complex either with a single needle or an array connected to a generator set at a selected frequency or modulating frequency range.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

The present invention relates to methods and systems for electrode placement for auricular peripheral nerve field stimulation (PNFS) using a unique method of anatomical visualization and percutaneous implantation of an electrode complex(s) designed as a needle array.

In one embodiment, the invention providers for a single use device that is physician applied for ambulatory, continuous, home based therapy. In one embodiment, the stimulator is percutaneously implanted into the cranial and/or peripheral nerves and corresponding neural vascular bundles of the auricular and periauricular areas as ascertained by the method of evaluating and implanting of the electrode/needle array provided in the present invention. This includes transillumination of the auricular and periauricular tissues and surrounding neurovascular anatomy. The auricular peripheral nerve stimulator system allows for continuous, intermittent neural stimulation.

In one embodiment, the auricular peripheral nerve stimulator system is a battery-operated, single-use device that has a preprogrammed frequency, pulse and duration for the stimulation of selected cranial and/or peripheral nerves and corresponding neural vascular bundles of auricular and periauricular areas. In one embodiment, the device power supply connects via three or more electrical conduit wires, sheathed in electrically insulating material, to one or more therapy electrode arrays comprised of multiple needles each and one reference electrode.

In another embodiment, the device comprises two or more needle arrays comprised of multiple needles each. In another embodiment, the device comprises three or more needle arrays comprised of multiple needles each. In another embodiment, the device comprises four or more needle arrays comprised of multiple needles each. In another embodiment, the needle arrays are comprised of two or more needles each. In another embodiment, the needle arrays are comprised of three or more needles each. In another embodiment, the needle arrays are comprised of four or more needles each. In another embodiment, the needle arrays are comprised of five or more needles each. In another embodiment, the needle arrays are comprised of six or more needles each.

Figures 1A, 1B:
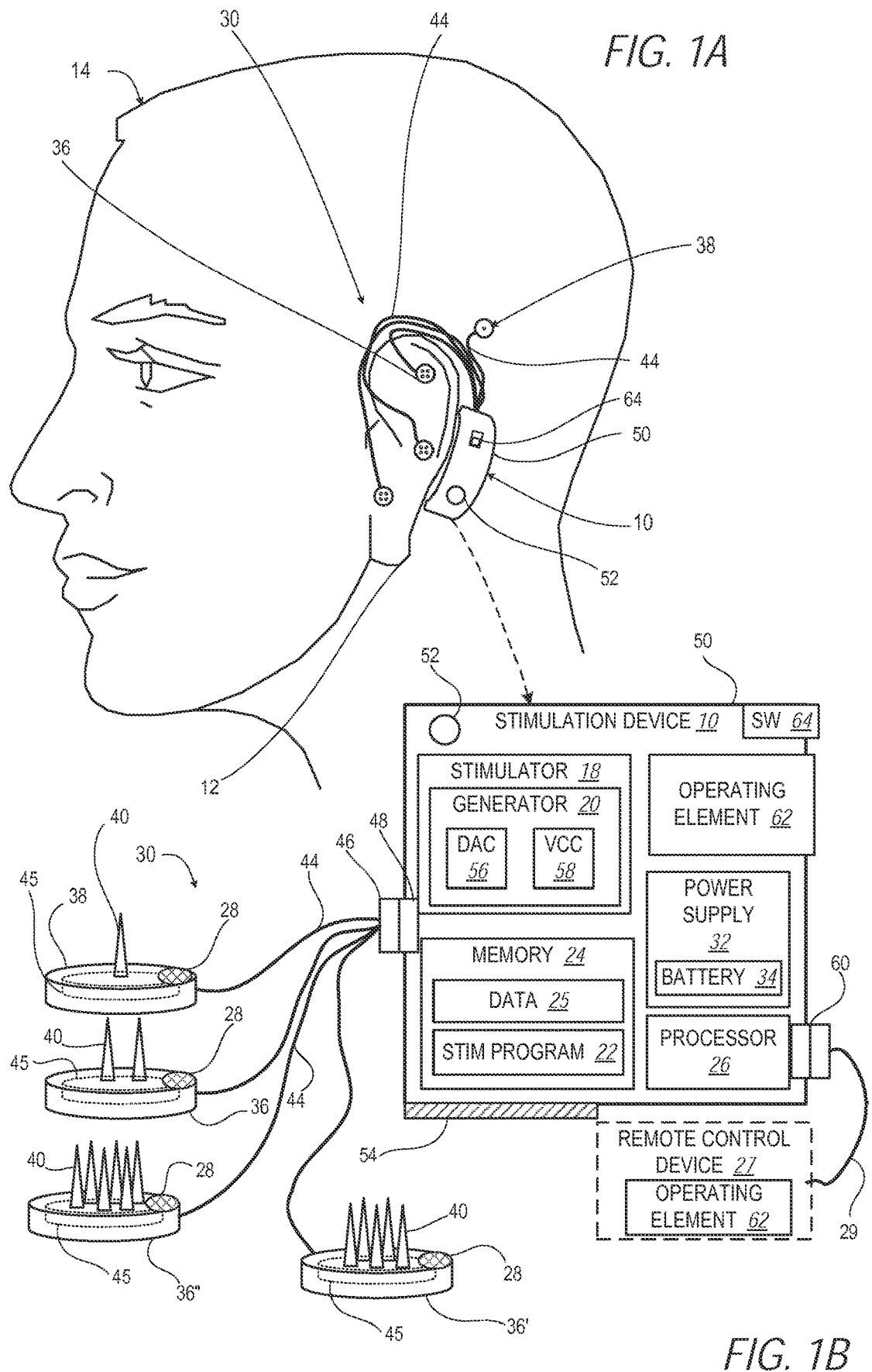
FIG. 1A is a side view of a head of a human being with an electrical stimulation device in an auricular application, according to one embodiment.
FIG. 1B is a block diagram of the electrical stimulation device of FIG. 1B, according to one embodiment.

Turning to the drawings, FIGS. 1A-1B depict an electrical stimulation device 10 for, in particular, an electrical acupuncture therapy in the region of an ear 12 of a human being 14. The stimulation device 10 includes a stimulator 18 containing a generator 20 for generating stimulation pulses with defined stimulation parameters, i.e. a defined voltage or a defined current, a defined duration, a defined repetition frequency and a defined duty cycle etc. In one embodiment, the electrical stimulation device 10 comprises an electrical signal generator 20 configured to generate electrical stimulation pulses having a repetition frequency of 0.5 to 100 Hz, preferably 1-10 Hz, and a duty cycle of 10 to 90%, preferably 40-60%. In one embodiment, the stimulation pulses are generated at a constant current amplitude.

With particular reference to FIG. 1B, electronic aspects of the electrical stimulation device 10 may be implemented by means of an analogue circuit, a digital circuit or a computer arrangement with a processor instructed by a suitable computer program, or any combination thereof. In one embodiment, a program 22 for performing stimulation is resident in memory 24 and executed by a microprocessor 26 to control the stimulator 18. The memory 24 may be implemented as several memory units of different types (RAM, ROM, etc.). The memory 24 stores instructions of a program 22 to allow a microprocessor 26 to perform one or more functions. Optionally, memory 24 stores a number of detected parameter values as obtained from detection devices 28, such as incorporated in an electrode needle array 30. The memory 24 may be any suitable memory 24 for storing a predetermined function such as a computer readable memory 24. The predetermined function may be a mathematical function or correlation. Suitable functions may be functions that are suitable for determining whether a determined parameter value is equal to, greater than or smaller than a predetermined threshold value. Based on his knowledge the skilled person will be able to determine suitable functions on the basis of which a response is required as a function of the determined parameter values. For example, the function may relate the absence of certain parameter values below a certain threshold value to a certain time frame. Such a function may be determined to detect the absence of breathing during a certain time period e.g. 1 second and longer, 2 seconds and longer or 5 seconds and longer.

Based on the program 22 as stored in the memory 24, the microprocessor 26 is able to process the number of detected parameter values as obtained from the detection device in said function. For this, the detected parameter values are loaded into the microprocessor 26 either directly from the detection devices 28 or alternatively from the memory 24 into which the detected parameter values were previously loaded. The function is loaded in the microprocessor 26 from the memory 24 or in an alternative embodiment the predetermined function may be embedded in said microprocessor 26. In the latter embodiment at least one memory 24 is (partially) integrated in the microprocessor 26. In one embodiment, the memory 24 records the stimulation parameters as a function of time as data 25 to enable the performance of a quality control check or check of the proper operation by a remote control device 27 that is periodically or permanently in communication with the stimulation device 10 via wireless or wired connection 29.

The detection device 28 may be any suitable device for detecting a number of parameter values. In the present specification, a "number" shall mean one or more unless explicitly stated otherwise. Parameters suitable for determining whether a subject is in need of resuscitation include but are not limited to parameters corresponding to muscle activity, parameters corresponding to breathing, or parameters corresponding to cerebral activity, such as electrical activity of neural cells including brain cells, or electrical activity recorded from the ear or any other suitable point on the body of a human being 14. Other sensors may be applied as well, like a sensor to measure body temperature, a sensor to measure pressure, and a sound sensor, like a microphone.

A power supply 32 is provided in order to supply the components of the stimulator 18 with electrical energy. In one embodiment, the power supply 32 is formed by a suitable battery 34 or an accumulator. The electrical pulses generated in the generator 20 of the stimulator 18 are delivered via at least one needle electrode array 30 comprising at least two therapy electrode arrays 36 and at least one ground or reference electrode 38.

Each therapy electrode 36 has two or more needle electrodes 40, which in an exemplary embodiment is four (4) in number. In one embodiment, the number of therapy electrodes 36 is selected from the group consisting of 2, 3, 4, 5, 6, 7, 8, 9, 10, or more. In another embodiment, the number of needle electrodes 40 per therapy electrode 36 is selected from the group consisting of 2, 3, 4, 5, 6, 7, 8, 9, 10, or more. In one embodiment, the number of needle electrodes 40 per therapy electrode 36 is 2-10. In one embodiment, the number of needle electrodes 40 per therapy electrode 36 is 3-9. In one embodiment, the number of needle electrodes 40 per therapy electrode 36 is 4-8. As seen in FIG. 1B, the array may include one or more therapy electrode 36' and 36", alone or in combination, with five (5) and six (6) needle electrodes 40, respectively.

The present invention has shown that the use of therapy electrode 36 having a plurality of two or more needle electrodes 40—and preferably 3 or more and more preferably 4 or more—provides for the unexpected result of a synergistic field effect and not merely an additive electrical stimulation for pain reduction.

Each reference electrode 38 includes at least at least one needle electrode 40. The therapy electrodes 36 and reference electrode 38 are inserted into the skin surface in the area to be stimulated. The reference electrode 38 provides a ground connection for electronic circuit located within the stimulator 18.

In one embodiment, the needle electrodes are made of an electrically conductive material, in particular a metal such as titanium, stainless steel or the like. In addition to metals, conductive synthetics are also conceivable for the production of the needle electrodes.

In one embodiment, the at least two needle electrodes 40 of the therapy electrode 36 are arranged in a common electrode housing 42 with a detection device 28 and connected to the stimulator 18 by an appropriate line 44. A circuit board 45 (FIG. 1B) on which the one or more needle electrodes 40 are mounted is arranged in the common electrode housing 42. The therapy electrodes 36 can, for instance, be simply connected to the circuit board 45 by a conductive adhesive. The line 44 is likewise connected to the circuit board 45, either by a solder joint or by a screw connection, the conductive tracks of the circuit board 45 safeguarding the electrical connection to the therapy electrodes 36. The arrangement of each therapy electrode 36 in a common electrode housing 42 provides for a defined distance between the individual needle electrodes 40. The line 44 for connecting the therapy electrodes 36 to the stimulator 18 can be fixedly, i.e. inseparably, or even detachably configured. Each line 44 can be fixedly connected respectively to the corresponding therapy electrode 36 or reference electrode 38. Each line 44 can also be fixedly connected to the stimulator 18. In the illustrative embodiment, each line 44 terminates at a plug 46 that is physically and electrically connected to a socket 48 mounted on an electronic housing 50 that contains the stimulator 18.

In order to attach the electronic housing 50 to the skin surface, a fastening element 54 (FIG. 1B), such as an adhesive element, may be provided. Besides the adhesive element, other fastening methods, e.g. via magnets, elastic bands or the like can be used. The fastening element can be integrated in the electrode housing. For example, the electronic housing 50 can adhesively mount behind the ear 12 of the human being 14 (FIG. 1A). The electronic housing 50, which may be made of a synthetic material and is preferably designed to be water-proof. The components depicted in FIG. 1A can be arranged in a preferably sterile package (not illustrated) so as to prevent any contamination of the needle electrode array 30.

The present invention provides an electrical stimulation system that provides unexpected results in terms of performance and efficacy. In one aspect, the present disclosure provides an electrical stimulation device 10 with a stimulator 18 containing a generator 20 for generating electrical stimulation impulses with defined stimulation parameters, and a power supply 32 for supplying the generator 20 with electrical energy, and with at least two needle electrodes 40 for insertion into the skin surface of an area that is to be stimulated.

In another aspect, the present disclosure provides an apparatus for stimulating auricular points on the human ear is provided using low voltage pulses that are generated and delivered by portions of the apparatus, particularly by percutaneously implanted needle electrodes into the cranial and/or peripheral nerves and corresponding neural vascular bundles of the auricular and periauricular areas.

In another aspect, methods of evaluating and implanting of the electrode/needle array include transillumination of the auricular and periauricular tissues and surrounding neurovascular anatomy.

Where the control device is coupled to operating elements for changing the stimulation parameters, manual adjustment and change of the stimulation parameters may be provided. Where no operating elements are provided, the respective adjustment of the stimulation parameters can be performed by programming the control device. To this end, the stimulator preferably comprises a suitable interface for connecting to a control computer.

An actuator or switch can be provided to activate the stimulator. Alternatively, the activation can, for instance, also be realized by removing an insulator on the battery 34 constituting the power supply 32.

In order to give a feedback on the operation of the stimulation device to the patient or the physician, an operation indicator 52, e.g. a light-emitting diode, can be provided in the stimulator. In addition to an optical operation indicator, an acoustic indicator of the proper operation or proper start-up can also be provided.

In another embodiment, the auricular peripheral nerve stimulator system is a battery-operated, single-use device that has a pre-programmed frequency, pulse and duration for the stimulation of selected cranial and/or peripheral nerves and corresponding neural vascular bundles of auricular and periauricular areas. The power supply 32 connects via four lines 44 of stainless steel wires, sheathed in a plastic overmolding, to three therapy electrodes 36 comprised of four (4) needle electrodes 40 each and one reference electrode 38 comprised of only one (1) needle electrode 40.

In another embodiment, the auricular peripheral nerve stimulator is a single use device that is physician applied for ambulatory, continuous, home based therapy. It is to be percutaneously implanted into the cranial and/or peripheral nerves and corresponding neural vascular bundles of the auricular and periauricular areas as ascertained by the disclosed method of evaluating and implanting of the electrode/needle array. This includes transillumination of the auricular and periauricular tissues and surrounding neurovascular anatomy. The auricular peripheral nerve stimulator system allows for continuous, intermittent neural stimulation for up to five days.

In another embodiment, the device is an ambulatory, physician applied, minimally invasive application of electrical neural stimulation implanted directed into the neurovascular bundles of the external ear verified by transillumination co joined with skin impedance measurement. In another embodiment, a generator located behind the ear, produces electrical stimulation impulses, which are transferred via an electrode/needle array to branches of cranial and/or occipital nerves and sympathetic fibers of the arterial branches.

In another embodiment, electrode/needle array implantation into the skin of the ear allows for direct access to branches of cranial nerves V, VII, IX, and X as well as branches of the occipital nerves. Direct access to the arterial branches of the head and neck are accessible and reduction of sympathetic stimulation results in an increase of vascular flow rate, reduction of vascular resistance and increase of perfusion. The arterial branches of the superficial temporal artery and the posterior auricular artery form a rich interconnecting complex network the terminal branches of which anastomose throughout the ear.

In another embodiment, the auricular peripheral nerve stimulator alters production and utilization of serotonin via vagal stimulation, and meningovascular dilation secondary to decreased sympathetic (or increased parasympathetic) tone.

In one embodiment, the device is powered by three lithium batteries, each with a voltage of 3 volts. In another embodiment, the device modulates a duty cycle between 2 hours on, 2 hours at rest. In another embodiment, the maximum performance time frame is 5 days or 120 hours (5 days×24 hours).

In another embodiment, the auricular peripheral nerve stimulator is a single use device that is physician applied for ambulatory, continuous, home based therapy. In another embodiment, it is to be percutaneously implanted into the cranial and/or peripheral nerves and corresponding neural vascular bundles of the auricular and periauricular areas as ascertained by the disclosed methods of evaluating and implanting of the electrode/needle array. The methods include transillumination of the auricular and periauricular tissues and surrounding neurovascular anatomy. In another embodiment, the auricular peripheral nerve stimulator system allows for continuous, intermittent neural stimulation for up to five days.

In one embodiment, the generator 20 for generating electrical stimulation pulses is comprised of a digital/analog converter (DAC) 56 and a voltage/current converter (VCC) 58. The therapy electrodes 36 are connected to the stimulator 18 via lines 44. The power supply 32 is preferably formed by a battery 34. The actuation of the generator 20, and the fixation of the stimulation parameters and control of the stimulation procedure, are effected via a control device, such as the microprocessor 26. The microprocessor 26 can be programmed, and its parameters can be changed, via an interface 60. A change in the stimulation parameters can also be effected manually by the aid of appropriate operating elements 62 coupled to the microprocessor 26 either on the electronic housing 50 or in the remote control device 27. The current amplitude of the stimulation pulses can, for instance, be adjusted and changed via operating elements 62, e.g. buttons. Activation of the stimulator 18 and the power supply 32 provided therein can be effected via a switch 64. In accordance with the invention, stimulation pulses are delivered to the lines 44 connected to the therapy electrodes 36 at constant current amplitudes in order to be more independent of the strongly varying impedance of the skin.

The stimulator 18 can store the stimulation parameters as data 25 in memory 24 as a function of time for subsequent examinations or for quality control. The memory 24 can be read out by an appropriate computer such as the remote control device 27 via the interface 60. To indicate the proper functioning of the electrical stimulation device 10 and the stimulator 18, respectively, an appropriate operation indicator 52 can be provided, which may, for instance, be formed by a light-emitting diode.

In some embodiments of the invention, the electrical stimulation device 10 comprises controls for the ability to adjust the voltage output to the therapy electrodes 36 by manipulation of controls. It is contemplated that in some instances the healthcare professional may wish to make changes to the voltage output to the devices of the present invention, such as the pulse frequency, the pulse width, the provision of sequential pulses, the output of more than one pulse at a time and the like. In one embodiment, variations in the operation of device are made using a serial interface. The term "serial interface" as used herein refers to device that may be coupled to the electronic circuit via an electrical port and to a computer or the like having software capable of being downloaded to the microprocessor 26 of the circuit. Once downloaded to the microprocessor 26, such software, such as program 22, would control the voltage output to the therapy electrodes 36, as desired.

The electrical stimulation device 10 can be operated for auricular use as follows. Initially, auricular points on the outer part of the ear 12 are identified depending upon the symptoms or other conditions of a particular patient. It should be appreciated that one skilled in the art can identify auricular points and/or their correlation with different health. Once such points are identified by a health care professional, the device of this invention is employed to deliver a pulsed voltage to such points.

Figures 2, 3:
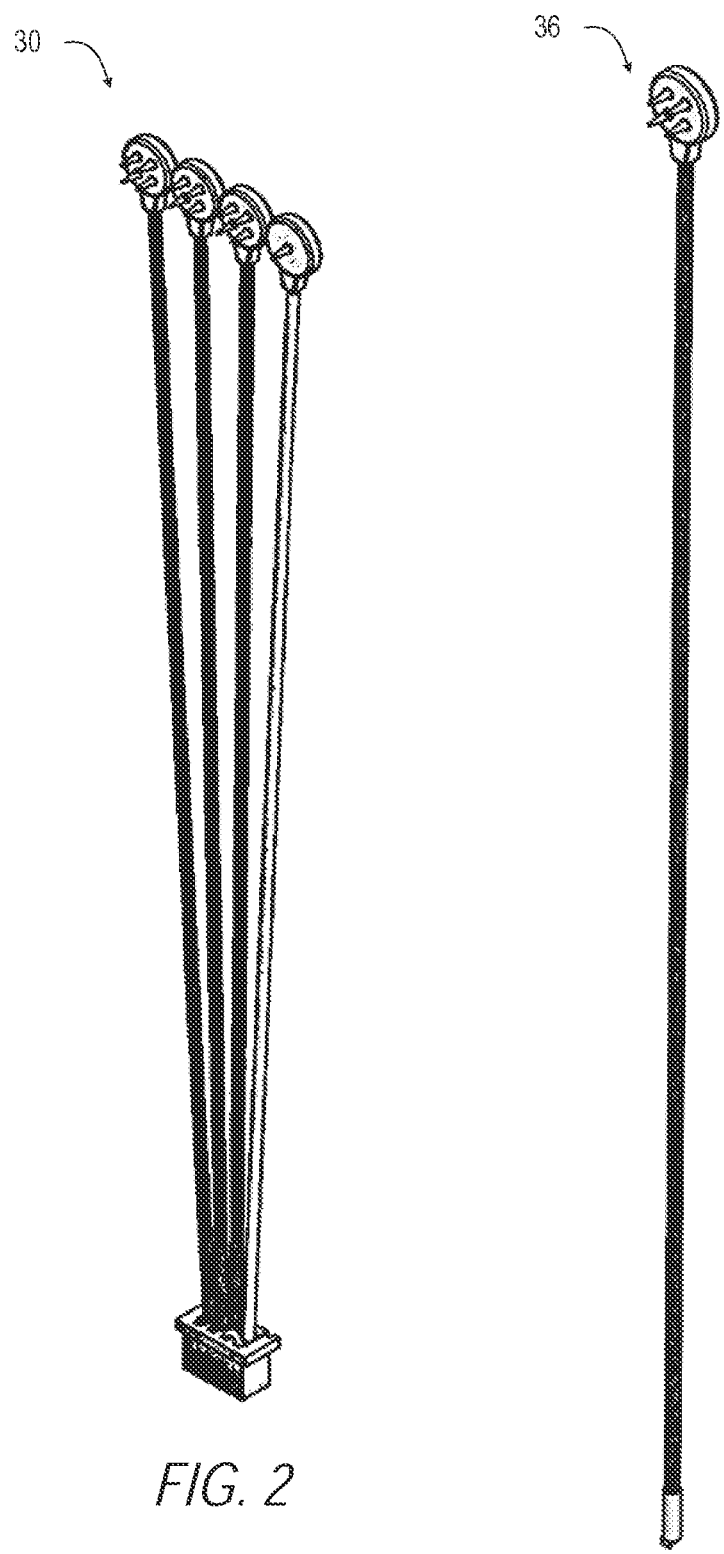
FIG. 2 is a perspective view of an electrode needle array of the electrical stimulation device of FIG. 1.
FIG. 3 is a perspective view of a single therapy electrode and line of the electrode needle array of FIG. 2, according to one embodiment.

FIG. 2 illustrates the electrode needle array 30 of the electrical stimulation device 10 of FIG. 1.

FIG. 3 illustrates a single therapy electrode 36 and line 44 of the electrode needle array 36 of FIG. 2.

Figure 4:
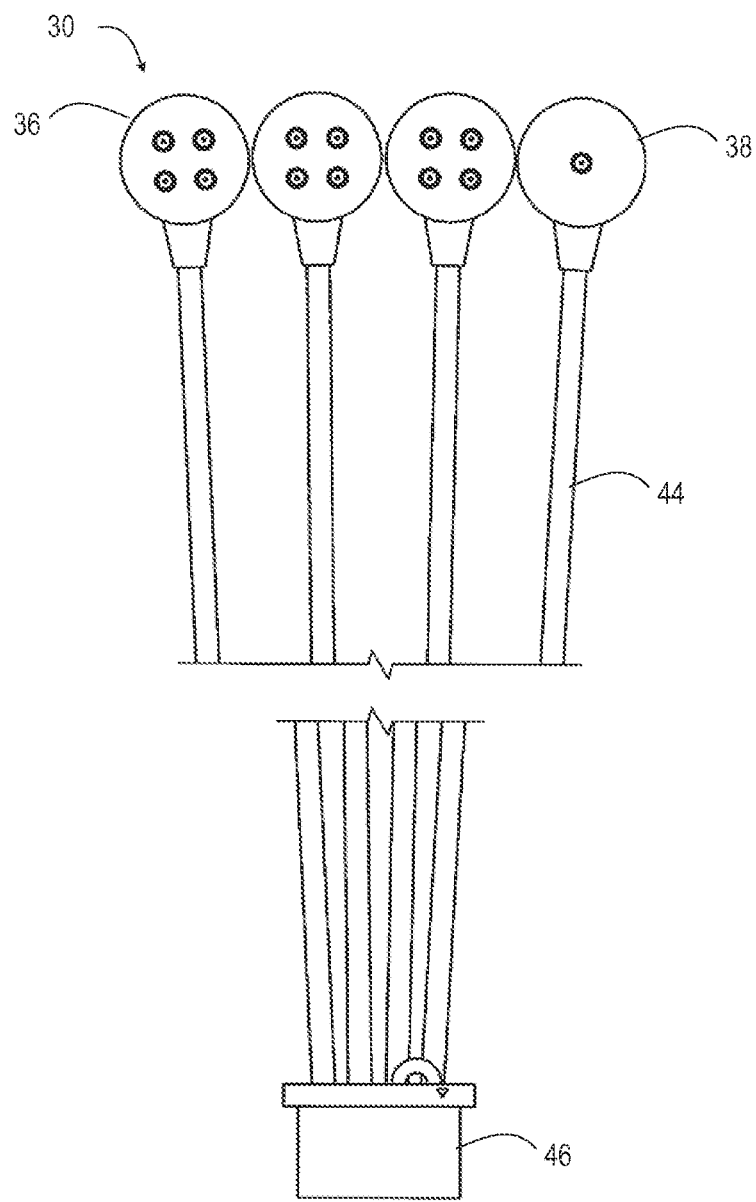
FIG. 4 is a front side view of the electrode needle array of FIG. 2, according to one embodiment.

FIG. 4 illustrates the electrode needle array 30.

Figures 5, 6, 7:
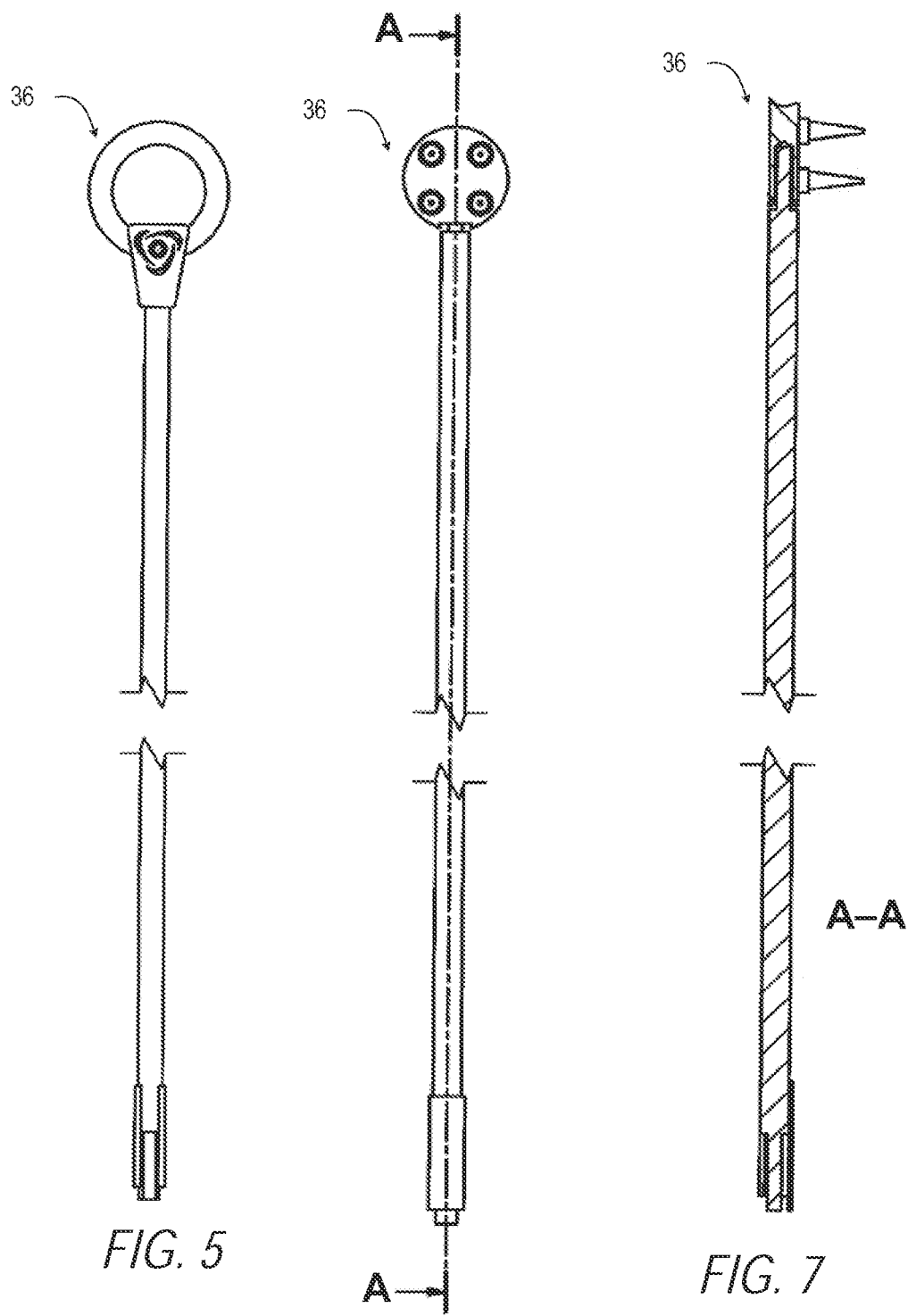
FIG. 5 is a back side view of the electrode needle array of FIG. 2, according to one embodiment.
FIG. 6 is a front side view of the single therapy electrode and line of FIG. 3, according to one embodiment.
FIG. 7 is a right side view of the single therapy electrode and line in a cross section view along lines A-A of FIG. 3, according to one embodiment.

FIG. 5 illustrates a back side view of the single therapy electrode 36.

FIG. 6 illustrates front side view of the single therapy electrode 36 and line 44.

FIG. 7 illustrates a right side view of the single therapy electrode 36 and line 44 in a cross section view along lines A-A of FIG. 3.

Figures 8, 9, 10, 11:
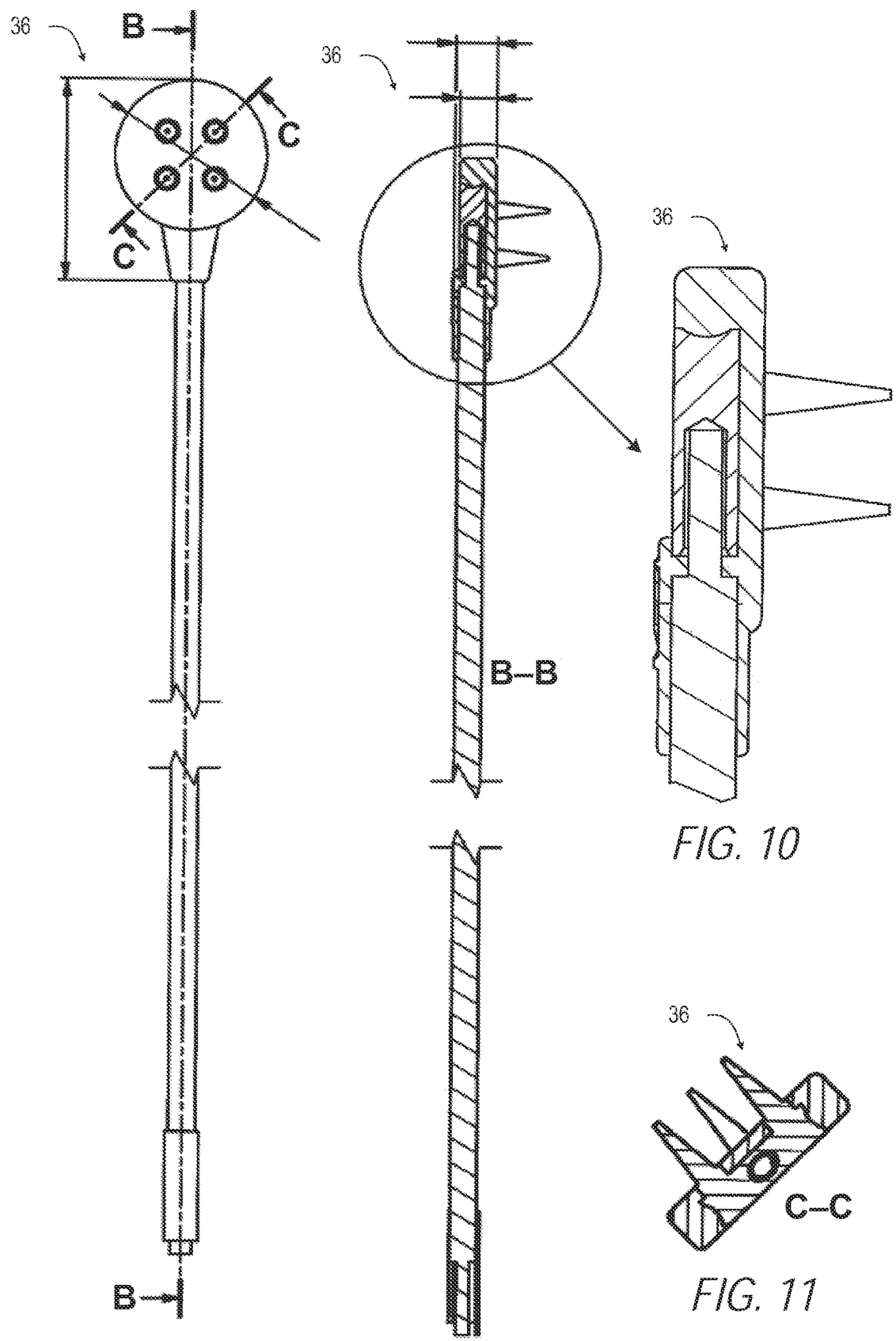
FIG. 8 is a front side view of the single therapy electrode and line of FIG. 3, according to one embodiment.
FIG. 9 is a right side view of the single therapy electrode and line in a cross section view taken along lines B-B of FIG. 8, according to one embodiment.
FIG. 10 is a right side detail view of the single therapy electrode of FIG. 9, according to one embodiment.
FIG. 11 is a top view of the single therapy electrode of FIG. 8 in cross section view taken along lines C-C, according to one embodiment.

FIG. 8 illustrates a front side view of the single therapy electrode 36 and line 44.

FIG. 9 illustrates a right side view of the single therapy electrode 36 and line 44 in a cross section view taken along lines B-B of FIG. 8.

FIG. 10 illustrates a right side detail view of the single therapy electrode 36 of FIG. 9.

Figure 12:
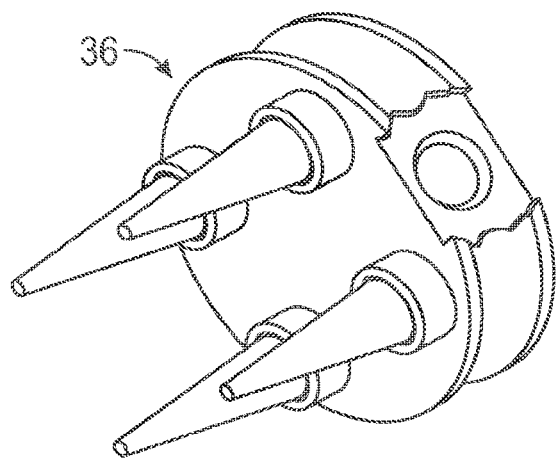
FIG. 12 is a perspective view of the single therapy electrode of FIG. 3, according to one embodiment.
Figure 13:
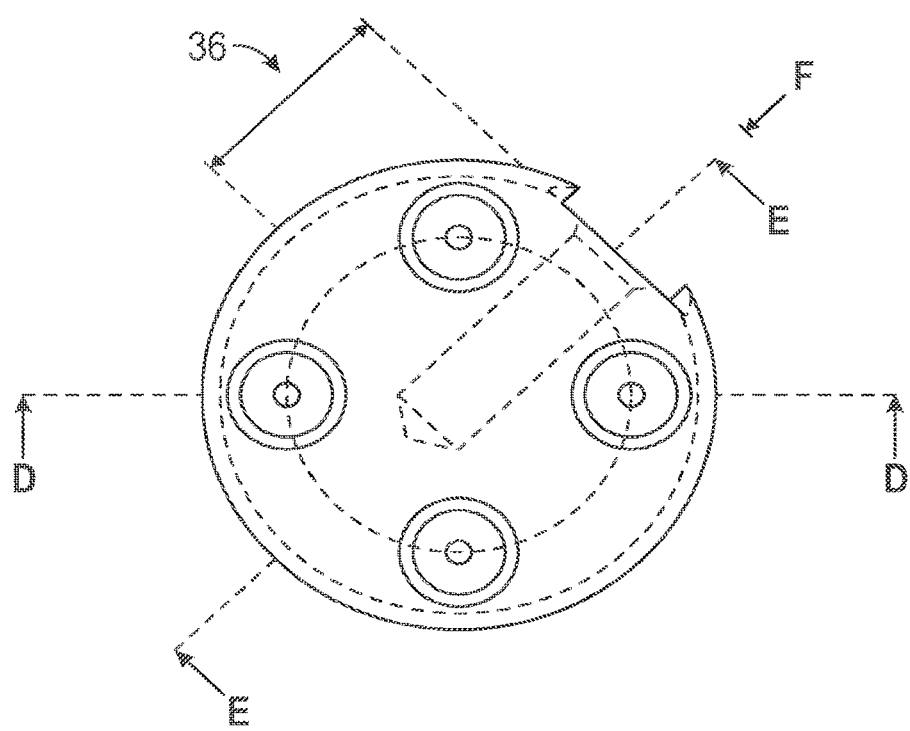
FIG. 13 is a side view of the single therapy electrode of FIG. 3 with a line port illustrated in phantom, according to one embodiment.

FIG. 11 illustrates a top view of the single therapy electrode 36 of FIG. 8 in cross section view taken along lines C-C, according to one embodiment;

FIG. 12 illustrates a perspective view of the single therapy electrode 36 of FIG. 3, according to one embodiment;

FIG. 13 illustrates a side view of the single therapy electrode 36 of FIG. 3 with a line port 66 illustrated in phantom, according to one embodiment.

Figure 14:
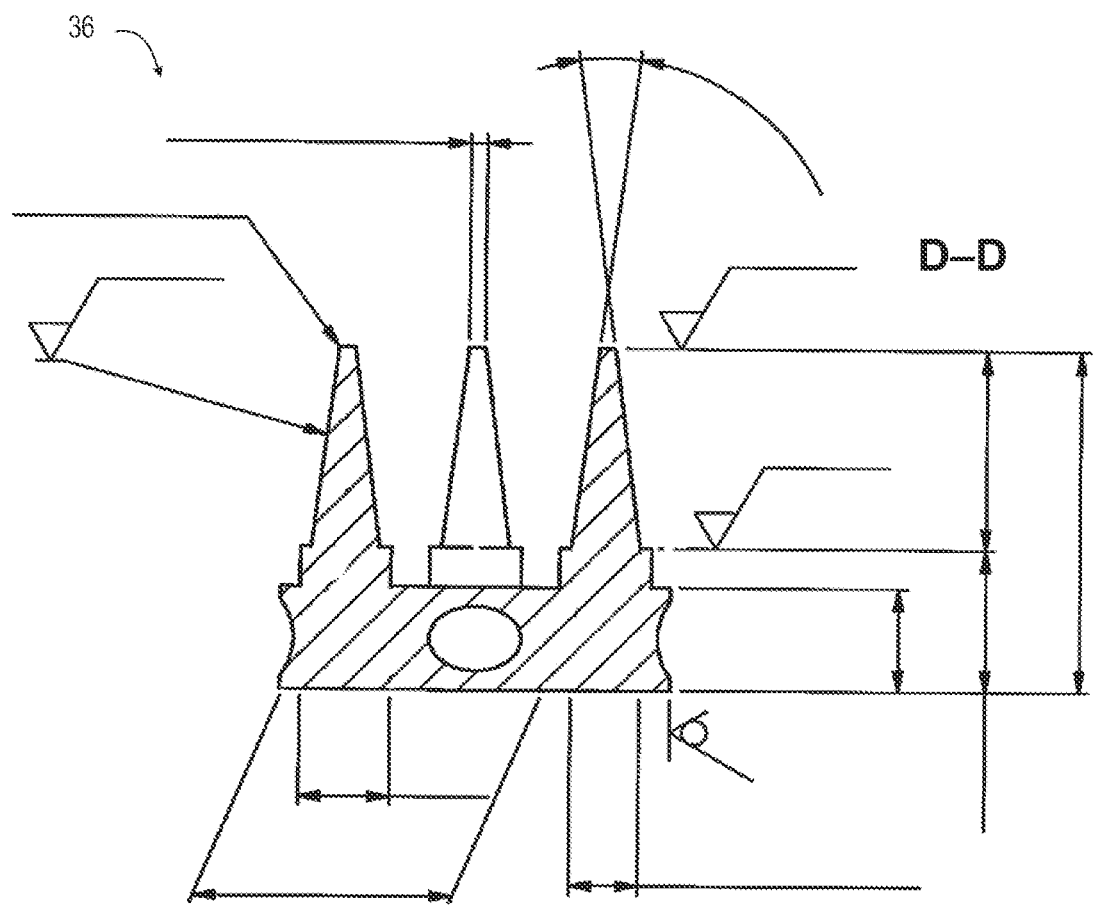
FIG. 14 is a side view of the single therapy electrode of FIG. 13 in cross section view taken along lines D-D, according to one embodiment.

FIG. 14 illustrates a side view of the single therapy electrode 36 of FIG. 13 in cross section view taken along lines D-D, according to one embodiment.

Figure 15:
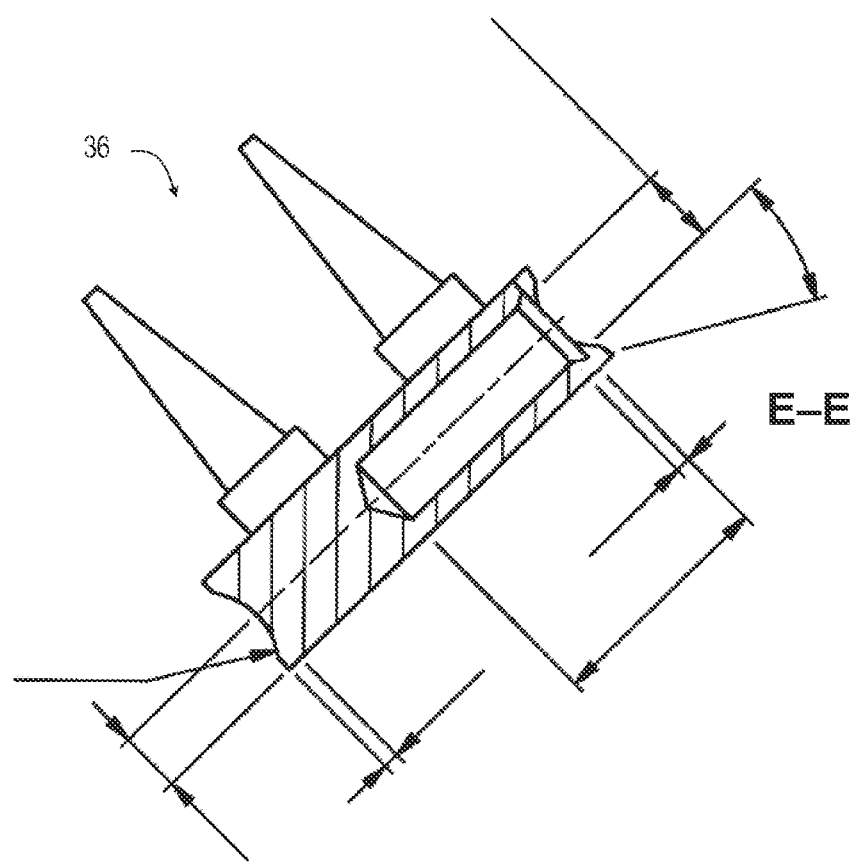
FIG. 15 is a side view of the single therapy electrode of FIG. 13 in cross section view taken along lines E-E, according to one embodiment.

FIG. 15 illustrates a side view of the single therapy electrode 36 of FIG. 13 in cross section view taken along lines E-E, according to one embodiment.

Figure 16:
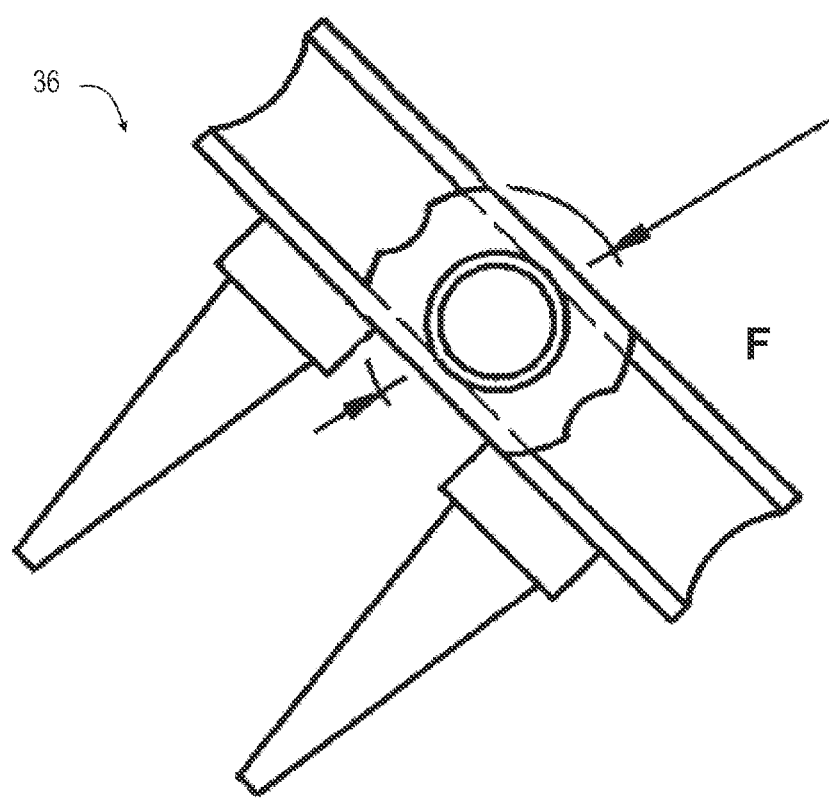
FIG. 16 is a side view of the single therapy electrode of FIG. 13 from a perspective of line F, according to one embodiment.

FIG. 16 illustrates a side view of the single therapy electrode 36 of FIG. 13 from a perspective of line F, according to one embodiment.

Figure 17:
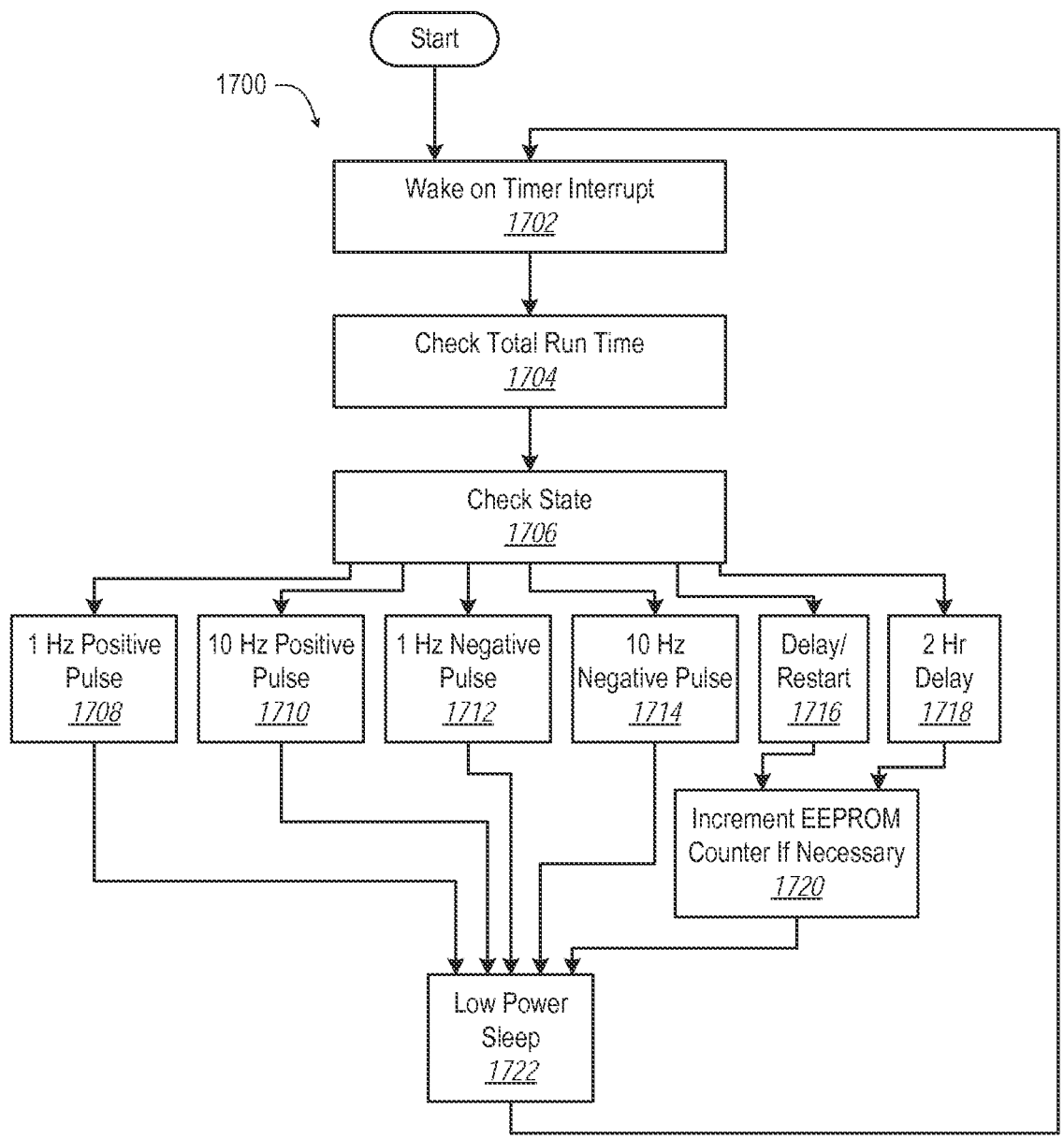
FIG. 17 is a flow diagram of a method of electrical stimulation using the electrical stimulation device of FIG. 1, according to one embodiment.

FIG. 17 illustrates a method 1700 of electrical stimulation using the electrical stimulation device 10 (FIG. 1). In one embodiment, the method 1700 includes the processor of the electrical stimulation device being awoken by a timer interrupt (block 1702). The processor checks a total run time (block 1704). As discussed below, the processor determines what state is appropriate for the current run time by checking state in block 1706. For example, the processor can prompt the generator to produce a 1 Hz positive pulse (block 1708). The processor can prompt the generator to produce a 10 Hz positive pulse (block 1710). The processor can prompt the generator to produce a 1 Hz negative pulse (block 1712). The processor can prompt the generator to produce a 10 Hz negative pulse (block 1714). The processor can determine that a delay timer has expired and restart time (block 1716) or the processor can delay of two hours is warranted (block 1718). Then the processor can increment an EEPROM counter if necessary (block 1720).

In one embodiment, the auricular peripheral nerve stimulator placement method comprises the steps:
 a) In some embodiments, the electrode/needle harness will be attached to the generator activating the device. Confirmation of successful activation may be tested by use of the provided ohmmeter to assure the circuit is complete.
 b) The subject's external ear will be chosen for application
 c) The chosen external ear and the anatomical location of the generator placement distal to the ear will be cleaned with an astringent to remove any surface oils or debris. Furthermore, the subject's external ear and the generator location may be disinfected by alcohol pads.
 d) The location of the auricular neurovascular bundles will be first visualized by the clinician using the transilluminator per protocol.
 e) The electrode/needle array connected to the lead wires are percutaneously implanted into the proper anatomical location being sure to penetrate the skin so implantation is percutaneous within 1 mm of the chosen neurovascular bundles.
 f) The duration of treatment is 120 hours.

In one embodiment, the electrically erasable programmable read-only memory (EEPROM) is updated each minute to ensure the unit repeats the pulse train for 2 hours, follows with a 2 hour low power delay cycle with no pulse output, then repeats the pulse and delays for a total of 120 hours regardless. EEPROM ensures run time data and the current action of the state machine are saved even if power is removed from the board. After 120 hours, all interrupts and timers are disabled and unit is allowed to go into an endless sleep state-effectively disabling the unit permanently.

The actual location and determination of needle placement (called points) is based upon tradition and theory of acupuncture. While the ascribed "points" may vary, depending upon the type of acupuncture to which one prescribes, the rationale and needle placement varies little and the theory is the same.

The addition of electrical stimulation to the individual, non-connected needles does not alter the rationale and the location of application is still based upon the original theory. The addition of electricity, while considered an enhancement, still falls within the realm of auricular acupuncture.

The present invention provides methods not based upon acupuncture technique or "points" but rather peripheral nerve field stimulation, anatomical location of cranial nerves, peripheral nerves, arterial branches and/or neurovascular bundles, and energy transfer based upon accepted laws of energy transfer in human tissue. Peripheral nerve field stimulation is an accepted procedure for the affecting of targeted nerves to alter pain transmission on a local (peripheral) and CNS (central nervous system) level. PNFS is commonly used in the occipital nerves (branches of the cervical nerves) for headache control, and the femoral nerve of the leg for control of phantom limb pain, stump pain, and other types of peripheral pain. The PNFS technique is based upon neuro-anatomy, blood vessel anatomy, proximity of the electrodes to the actual nerves being stimulated, and verification of electrode proximity.

Without wishing to be bound by theory, the method of auricular application of PNFS relies on the fact that located within the ear are cranial nerves V, VII, IX, X which anastomose (connect) directly into the brain and branches of the greater and lesser occipital nerves anastomosing directly into the cervical spine. There are distinct areas of the auricle on both the dorsal and ventral aspect which carry a predominance/concentration of the cranial nerves, peripheral nerves, arterial branches, and neurovascular bundles.

Branches of the superior temporal artery and the posterior auricular artery are found within the external ear, entering from the anterior (ventral) and posterior (dorsal) aspect of the ear. These arteries converge in the lobe, branching eventually into the cellular level forming a complex, interconnecting network branching according to Mandelbrot's set.

These physical entities can be selectively targeted by percutaneous implantation of one or more electrode/needle complex(s) either with a single needle or an array connected to a generator set at a selected frequency or modulating frequency range.

The nerves and arteries converge into neurovascular bundles. Visualization of the bundles can be achieved by transillumination of the ear, ultrasonic imaging or other techniques used to visualize or infer these particular kinds of anatomy.

Application of these procedures, it's rationale, and verification are unique to our technique and varies from the previously held concepts of auricular acupuncture in the following manner:
 a) The verification of the bundles is ascertained by physical anatomy and visualization.
 b) There are anatomical areas, which have concentrations of the cranial nerves and arterial branches but no set "points" to learn and follow. Location of placement of the electrode/needle complex must be individualized and is not "pre set".

c) The theory is based on neurovascular stimulation and targeted stimulation of the cranial nerves or peripheral nerves, not acupuncture points (chi, hot/cold, or reflex points).

This is accomplished due to the thickness of the tissue of the external ear is thin enough that a focused light (transilluminator) can pass through the tissue (transillumination). Also, there is a difference in density between the auricular tissues and the auricular neurovascular bundles allowing the bundles to be visualized and outlined. Finally, both measurement of the rate of arterial blood flow and the vessel anatomy can be visualized and isolated using ultra sonic imaging and other techniques used to directly visualize neurovascular or vascular tissues.

The electrode/needle complex(s) are implanted percutaneously to stimulate the arterial branches, the cranial nerves, peripheral nerves and the neurovascular bundles. There is a natural tissue resistance to electricity. The implantation must be within 2 mm of the nerve and vascular tissue to have an effect. The implanted needle cannot be directly into an arterial branch. Percutaneous implantation of one or more needle/electrode complex(s) or an array beyond the capability of the tissue to transfer the electricity will cause tissue damage and pain with little or no energy transfer to the neurovascular bundles, arterial branches, peripheral or cranial nerves. Percutaneous implantation of a needle or needle/array directly into a main arterial branch will cause pain and bleeding. This application technique/method and energy transfer is based on both Coulomb's law and Ohm's law.

The verification of the cranial nerves, peripheral nerves, arterial branches, and neurovascular bundles are ascertained by anatomy and visualization. There are anatomical areas (zones), which have predictable and reproducible concentrations of the cranial nerves, peripheral nerves, arterial branches, and neurovascular bundles but no set "points" to learn and follow. Electrode/needle implantation must be within parameters of the electrode design, generator design, and tissue resistance as determined by Coulomb's and Ohm's laws. The combination of the understanding of anatomy, visualization, and proper percutaneous implantation of the needle/electrode array will determine proper transfer of the electricity into the neurovascular bundles. Without using this unique method, the electrode/needle implantation into the auricle is not accurate.

In one embodiment, the application method can be performed as follows:

Clean off the skin of the dorsal and ventral of the ear with an astringent. This removes surface oils, make up, etc. which may interfere with implantation and energy transfer from the generator.

Using a transilluminator, ultrasonic imaging, or other visualization techniques, the area (zone) into which there is a concentration of cranial nerves, occipital nerves, neurovascular bundles, and branches of the superficial temporal and posterior auricular arteries are targeted as per our guidelines. Choose the area that corresponds to the neuroanatomy, which is to be targeted.

In one embodiment, transillumination technique can be performed as follows:
a) Place the lighted, optic tip of the transillumination device directly against the skin on the ventral or dorsal aspect of the ear at 90 degrees so the concentrated light passes through the tissue. The light can be a direct, focused light or an array of lights of any color spectrum. Since the light passes through the tissue and the auricular tissue has a different density than the neurovascular bundles, this will in essence outline the arterial branches and the neurovascular vascular bundles so they can be seen.
b) Implant the needle/electrode complex(s) percutaneously within 2 mm of the neurovascular bundles (as visualized) but not directly into an arterial branch by placing the needle into the skin at 90 degrees from either the dorsal or ventral aspect of the ear depending upon which of the cranial nerves, occipital nerves, neurovascular bundles, or arterial branches are to be targeted. The needle should not be inserted directly into a main arterial branch. The needle must pass through the outer dermis to be classified as percutaneous. Placing any type of stimulation to the outer skin without complete skin penetration is considered transcutaneous.
c) Verification of correct placement is by determined by patients noting the pulsing of the electricity, and/or enlarging of the associated arteries by unaided visual inspection. In one embodiment, the method further comprises following up with transillumination as per described protocol to help verify arterial reaction. In another embodiment, the method further comprises measurement of an increase in blood flow, as measured or determined by any method or device All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. An auricular peripheral nerve field stimulator, comprising:
   at least one therapy electrode configured for percutaneous insertion into an auricle of a human ear near at least one nerve located therein, and
   an electrical stimulation device electrically coupled to the at least one therapy electrode, the electrical stimulation device programmed to generate and deliver electrical stimulation signals while in use to at least one therapy electrode
   the electrical stimulation comprising defined stimulation parameters, the defined stimulation comprising at least a defined pulse frequency and at least one of a defined pulse width or a defined duty cycle.

2. The auricular peripheral nerve field stimulator of claim 1, wherein the defined stimulation parameters further comprises at least one of a defined signal amplitude and a defined signal repetition frequency.

3. The auricular peripheral nerve field stimulator of claim 1, further comprising means for attaching the housing to or adjacent to the human ear.

4. The auricular peripheral nerve field stimulator system of claim 1, further comprising one of a battery and an accumulator electrically coupled to the electrical stimulation device to supply the electrical stimulation device with electrical energy.

5. The auricular peripheral nerve field stimulator of claim 1, further comprising a remote control device,
   wherein operation of the electrical stimulator device is controllable via the remote control device.

6. The auricular nerve field stimulation device of claim 2, wherein the defined stimulation parameters comprise the defined signal amplitude, and the defined signal amplitude is a constant current amplitude.

7. The auricular nerve field stimulation device of claim 1, further comprising a reference electrode carrying at least one needle electrically coupled to the electrical stimulation device and configured for percutaneous insertion into a skin surface of or near the human ear, the at least one needle of the reference electrode providing a reference for the electrical stimulation signals.

8. The auricular nerve field stimulation device of claim 1, wherein the defined stimulation parameters further comprise at least one of a defined stimulation signal duration and a total therapy duration during which the electrical stimulation signals are generated and delivered by the electrical stimulation device.

9. The auricular nerve field stimulation device of claim 1, wherein the at least one therapy electrode includes at least one needle configured for percutaneous insertion into the auricle.

10. The auricular nerve field stimulation device of claim 1, wherein the at least one therapy electrode comprises a plurality of therapy electrodes each electrically coupled to the electrical stimulation device and each including at least one needle configured for percutaneous insertion into the auricle.

11. A method for auricular peripheral nerve field stimulation, the method comprising:
    directing a user to locate at least one auricular neurovascular bundle within an auricle of a human ear,
    directing the user to percutaneously insert at least one needle, carried by at least one therapy electrode, into the auricle near the at least one located auricular nerve,
    directing the user to electrically couple an electrical stimulation device to the at least needle of the at least one therapy electrode, and
    directing the user to activate an electrical stimulation device to generate and deliver electrical stimulation signals with defined stimulation parameters, the defined stimulation parameters comprising a defined pulse frequency and at least one of a defined pulse width or a defined duty cycle.

12. The method of claim 11, wherein the defined stimulation parameters comprise at least one of a defined signal amplitude and a defined signal repetition frequency.

13. The method of claim 11, wherein directing the user to percutaneously insert the at least one needle carried by the at least one therapy electrode into the auricle comprises directing the user to percutaneously insert the at least one needle into a ventral or dorsal aspect of the auricle within about 2 mm of the located neurovascular bundle.

14. The method of claim 11, further comprising directing the user to control operation of the electrical stimulation device with a remote control device.

15. The method of claim 12, wherein the defined stimulation parameters comprise the defined signal amplitude, and the defined signal amplitude is a constant current amplitude.

16. The method of claim 11, further comprising providing a reference for the electrical stimulation signals with a reference electrode carrying at least one needle electrically coupled to the electrical stimulation device, and percutaneously inserting the at least one needle carried by the reference electrode into a skin surface on or near the human ear.

17. The method of claim 11, wherein the defined stimulation parameters further comprise at least one of a defined stimulation signal duration and a total therapy duration during which the electrical stimulation signals are generated and delivered by the electrical stimulation device.

18. The method of claim 11, wherein directing the user to activate an electrical stimulation device comprises directing the user to activate an electrical stimulation device to generate and deliver the electrical stimulation signals in the form of a pulse train having a repetition frequency of at least one of +1 Hz, −1 Hz, +10 Hz and −10 Hz.

19. The method of claim 11, wherein directing the user to activate an electrical stimulation device comprises directing the user to activate an electrical stimulation device to generate and deliver the electrical stimulation signals in the form of a pulse train having a repetition frequency of between about 0.5 Hz to 100 Hz.

20. The method of claim 11, wherein directing the user to percutaneously insert at least one needle comprises directing the user to percutaneously insert at least one needle of each of a plurality of therapy electrodes into the auricle each near one or more located auricular neurovascular bundles within the auricle,
- wherein directing the user to electrically couple an electrical stimulation device to the at least needle comprises directing the user to electrically couple the electrical stimulation device to the at least one needle of each of the plurality of therapy electrodes,
- and wherein directing the user to control the electrical stimulation device to generate and deliver electrical stimulation signals to the percutaneously inserted at least one needle comprises directing the user to control the electrical stimulation device to generate and deliver electrical stimulation signals to the percutaneously inserted at least one needle of each of the plurality of therapy electrodes.

* * * * *